United States Patent [19]
Su et al.

[11] Patent Number: 5,629,202
[45] Date of Patent: May 13, 1997

[54] COMPUTER-CONTROLLED BIOREACTOR SYSTEM FOR ENZYMATIC SYNTHESIS OF L-TRYPTOPHAN

[75] Inventors: Chein-Shyong Su; Zen-Jen Chan; Wuen-Hsian Huang; Hsin Tsai, all of Taipei, Taiwan

[73] Assignee: Development Center for Biotechnology, Taipei, Taiwan

[21] Appl. No.: 467,523

[22] Filed: Jun. 6, 1995

Related U.S. Application Data

[62] Division of Ser. No. 277,481, Jul. 19, 1994.

[51] Int. Cl.$^6$ ................................................. C12M 1/36
[52] U.S. Cl. ................................ 435/286.5; 435/286.7; 435/288.7
[58] Field of Search ........................... 435/3, 4, 26, 108, 435/286.1, 286.5, 288.7, 289.1, 808, 286.7

[56] References Cited

U.S. PATENT DOCUMENTS

| | | | |
|---|---|---|---|
| 4,335,209 | 6/1982 | Asai et al. | 435/108 |
| 4,349,627 | 9/1982 | Mimura et al. | 435/108 |
| 4,360,594 | 11/1982 | Mimura et al. | 435/108 |
| 4,761,374 | 8/1988 | Beppu et al. | 435/232 |

FOREIGN PATENT DOCUMENTS

| | | |
|---|---|---|
| 2379603 | 10/1978 | France. |
| 2581654 | 11/1986 | France. |
| 56-85291 | 7/1981 | Japan. |
| 62-134094 | 6/1987 | Japan. |
| 63-137689 | 6/1988 | Japan. |
| 64-51093 | 2/1989 | Japan. |
| 1-104186 | 4/1989 | Japan. |
| 1-191692 | 8/1989 | Japan. |
| 90/01553 | 2/1990 | WIPO. |

OTHER PUBLICATIONS

Perry, "Perry's Chemical Engineering Handbook." McGraw–Hill, USA, 1984, pp. 27–14 to 27–17.
Blanch, et al., "Enzyme Bioreactors Employing Reverse Michelles and Two–Phase Systems", *International Bioreactors Symposium, 8th*, 1:577–590 (1988).
Abstract of Vorlop, et al., "Use of Gas Sensor Systems in Bioreactor Control—e.g. During Ethanol or Tryptophan Production; Systems Control".
Abstract of Japanese Patent 1104186 dated Apr. 1989.
Abstract of French Patent 2581654, dated Nov. 1986.
Abstract of Japanese Patent 5685291 dated Jul. 1981.
Abstract of Japanese Patent 62134094 dated Jun. 1987.
Abstract of Japanese Patent 63137689 dated Jun. 1988.
Abstract of Japanese Patent 6451093 dated Feb. 1989.
Abstract of Japanese Patent 1191692 dated Aug. 1989.

*Primary Examiner*—William H. Beisner
*Attorney, Agent, or Firm*—Campbell & Flores LLP

[57] ABSTRACT

Disclosed is an automatic computer-controlled bioreactor system for enzymatic synthesis of L-tryptophan which comprises a bioreactor linked to a computer equipped with an on-line indole assay device, in which the computer controls the feeding of indole, pyruvic acid and/or its salt and an ammonium salt into the bioreactor and feedback-controls the reaction in the bioreactor by indole concentration determined by the on-line indole assay device, wherein the feeding of indole and ammonium salt is controlled by a pre-defined profile that agrees with a tryptophanase activity profile and pyruvic acid and/or its salt is added at a predetermined time.

13 Claims, 4 Drawing Sheets

COMPUTER-CONTROLLED BIOREACTOR SYSTEM FOR ENZYMATIC SYNTHESIS OF L-TRYPTOPHAN

This application is a divisional of application Ser. No. 08/277,481, filed Jul. 19, 1994.

FIELD OF THE INVENTION

The present invention relates to a process for enzymatic synthesis of L-tryptophan using an automatic computer-controlled bioreactor system and to the computer-controlled bioreactor system thereof.

BACKGROUND OF THE INVENTION

Tryptophan is one of the essential amino acids constituting the bodies of animals, and is important as a medicine, nutrient, or as an additive for animal feed. Known methods for producing tryptophan include fermentation processes and enzymatic processes. For fermentation processes, tryptophan could be produced from its precursors either by adding anthranilate or indole with sugar to a culture, or by direct fermentation of glucose in the culture. For enzymatic processes, tryptophan could be produced from indole, pyruvic acid and ammonium ion by using a microorganism-produced tryptophanase. An enzymatic process has the advantage that a simpler process for purification and higher purity of tryptophan are achievable and such process has become a method of choice for producing the medicinal grade of L-tryptophan.

In the production of L-tryptophan using bacteria producing high levels of tryptophanase, one of the substrate indole is toxic to bacteria and causes substrate inhibition even at low concentration (18 mM). It is therefore disadvantageous to use the indole concentration as the driving force for the synthetic reaction. Also, tryptophan over 50 mM causes product inhibition and sodium pyruvate decomposes in the presence of NH4$^+$ ion at alkaline pH (pH 9.0). As a result, methods of producing L-tryptophan at high concentration could be obtained by continuous or stepwise feeding of concentrated indole to maintain limiting concentration of indole, and with the help of tryptophan precipitant—inosine, higher concentration of L-tryptophan (>80 g/L) is achievable.

There are many known methods for producing L-tryptophan using tryptophanase. Japanese Patent 56085291 describes production of L-tryptophan by reacting indole with serine or with pyruvic acid and ammonium ion using strain of genus Aeromonas, Vibrio or Bacillus. U.S. Pat. No. 4,349,627 describes a method wherein L-tryptophan is produced from indole and serine or from indole, pyruvic acid, and ammonium ion with a particular microorganism of genus Enterobacter. Tryptophanase producing strains including *Proteus rettgeri, Proteus vulgaris, Proteus mirabilis, Proteus morganil* and *Escherichia coli* were used to prepare L-tryptophan in Japanese Patent 62134094. Japanese Patent 63137689 describes using heat treated microorganisms including various species of *Escherichia coli* to prepare L-tryptophan from indole, pyruvic acid and ammonium ion.

Japanese Patent 1104186 describes a method of producing L-tryptophan from indole and L- or D,L-serine using tryptophan synthase. French Patent 2581654 describes a method of reacting indole with pyruvate and ammonium ion by immobilized tryptophanase and recovering L-tryptophan by precipitation with inosine. Japanese Patent 64051093 describes a method of preparing L-tryptophan using tryptophanase with stepwise feeding of indole to maintain its concentration below 4 mM and 39 mM of L-tryptophan can be produced in 10 hours of reaction. Japanese Patent 01191692 describes a process using immobilized cell to prepare L-tryptophan from indole and pyruvic acid wherein indole is continuously fed to maintain at 17 mM and L-tryptophan is continuously or stepwisely removed by a separator, 36.49 g of L-tryptophan can be obtained in 120 hours of operation from 1 L of reactor in which the fractional conversion of indole and pyruvate is 92% and 84%, respectively., European Patent 381744 describes a multi-stage process for the production of L-tryptophan where a bacterial host cell was transformed to include tryptophanase which was then used in a subsequent bioconversion stage to accumulate L-tryptophan by continuously controlled feeding of indole to maintain its concentration below 10 mM in a batch reaction and 24 g/L of L-tryptophan was produced in 75 minutes, which gave over 99% fractional conversion of indole.

Although inexpensive raw materials such as ammonia can be used to synthesize L-tryptophan with indole and pyruvate that are of economic advantages, there are always many serious problems in the process such as indole inhibition, L-tryptophan inhibition and decomposition of pyruvate. To date, there are some enzymatic processes that produce L-tryptophan in rather high yield and high rate by controlled feeding of indole and/or pyruvic acid, but there is no report concerning feeding of indole, pyruvate and NH$_4$Cl by on-line feedback control operated simultaneously.

In addition to the known problems, a phenomenon has been observed in this invention that except under optional conditions, tryptophanase will decay when it is incubated with two of the substrates—sodium pyruvate and NH$_4$Cl. In order to overcome the above problems, feeding of indole, sodium pyruvate, and NH$_4$Cl is controlled by a computer equipped with an on-line indole assay device of this invention. The computer controls the feeding of indole and NH$_4$Cl by a pre-defined profile that agrees with a tryptophanase activity profile. Sodium pyruvate is added at a predetermined time during the reaction. The product inhibition is overcome by addition of L-tryptophan precipitant—inosine which can remove L-tryptophan from reaction system through forming an insoluble complex with L-tryptophan. The combination of feedback control of substrate feeding together with the introduction of inosine into the reaction vessel results in a high efficient process for enzymatic synthesis of L-tryptophan.

SUMMARY OF THE INVENTION

According, it is an object of the present invention to provide a process for enzymatic synthesis of L-tryptophan using an automatic computer-controlled bioreactor system to control the feeding of indole, pyruvic acid and/or its salt and an ammonium salt, and feedback-control the reaction.

Another object of the subject invention is to provide a process for enzymatic synthesis of L-tryptophan which comprises reacting indole with pyruvic acid and/or its salt and an ammonium salt in the presence of tryptophanase using an automatic computer-controlled bioreactor system comprising a bioreactor linked to a computer equipped with an on-line indole assay. device, in which the computer controls the feeding of indole, pyruvic acid and/or its salt and an ammonium salt into the bioreactor and feedback-controls the reaction in the bioreactor by indole concentration determined by the on-line indole assay device, wherein the feeding of indole and ammonium salt is controlled by a pre-defined profile that agrees with a tryptophanase activity profile and pyruvic acid and/or its salt is added at a predetermined time.

A further object of the subject invention is to provide an automatic computer-controlled bioreactor system for use in enzymatic synthesis of L-tryptophan which comprises a bioreactor linked to a computer equipped with an on-line indole assay device, in which the computer controls the feeding of indole, pyruvic acid and/or its salt and an ammonium salt into the bioreactor and feedback-controls the reaction in the bioreactor by indole concentration determined by the on-line indole assay device, wherein the feeding of profile that agrees with a tryptophanase activity profile and pyruvic acid and/or its salt is added at a predetermined time.

These and other objects, advantages and features of the present invention will be more fully understood and appreciated by reference to the written specification.

DETAILED DESCRIPTION OF THE INVENTION

Figure 1:
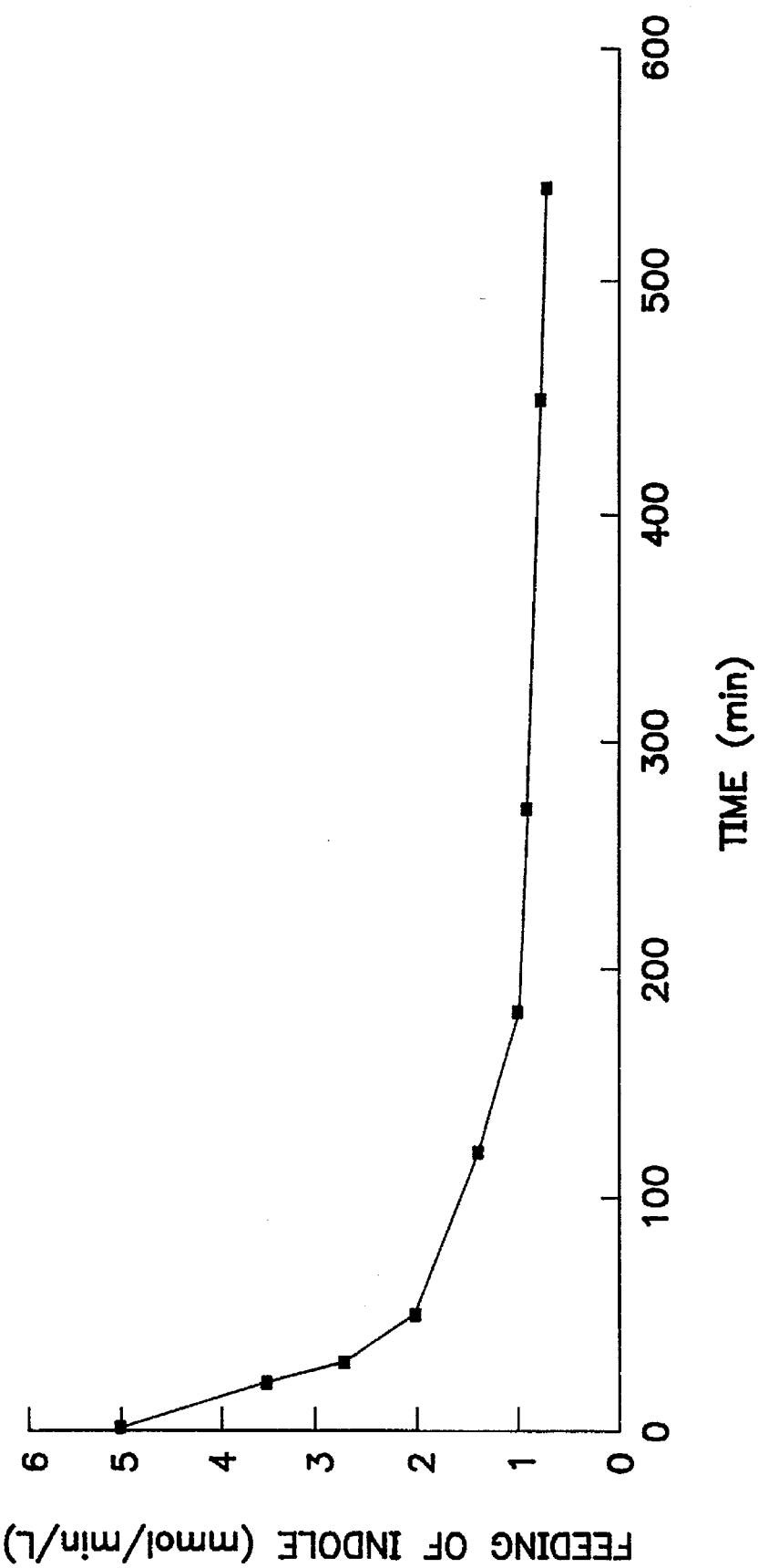
FIG. 1 shows feeding profile of substrates in enzymatic synthesis of L-tryptophan using computer-controlled multi-slope feeding of indole. Bioreactor initial conditions are as follows: 48, 60, 72 mmole of $NH_4Cl$, Na-pyruvate, and inosine, respectively; 1g wet cell in 120 mL scale.

The invention relates to a novel process for the enzymatic preparation of L-tryptophan. High amount of L-tryptophan (>100 g/L) could be obtained by the accumulation reaction catalyzed by tryptophanase in a batch type bioreactor in the presence of inosine. A newly designed automatic computer-controlled bioreactor system comprising an on-line indole assay and feedback control of feeding is established and optimal reaction profiles are determined. A typical batch reaction at 600 mL scale using crude enzyme would give successful results, for example, about 66.2 g (324 mmole) of L-tryptophan was obtained from 38.3 g (327 mmole) indole, 50.8 g (462 mmole) sodium pyruvate and 104.6 g (390 mmole) inosine within 4 hours. The whole operation can be automatically computer-controlled.

In this invention, a batch type bioreactor comprising continuous automatic feeding of indole, pyruvic acid and/or its salt and an ammonium salt by computer is designed and operated to give an optimal reaction condition. By this system, a rather high titre (>100 g/L) of L-tryptophan can be achieved and over 96% conversion of indole and 65–82% conversion of pyruvate can be maintained. The L-tryptophan-inosine complex obtained could be easily separated by filtration for further purification and inosine could be recycled for use. This is a new and advantageous system for industrial production of high purity of L-tryptophan.

The process comprises reacting indole with pyruvic acid and/or its salt and an ammonium salt in the presence of tryptophanase using an automatic computer-controlled bioreactor system comprising a bioreactor linked to a computer equipped with an on-line indole assay device, in which the computer controls the feeding of indole, pyruvic acid and/or its salt and an ammonium salt into the bioreactor and feedback-controls the reaction in the bioreactor by indole concentration determined by the on-line indole assay device, wherein the feeding of indole and ammonium salt is controlled by a pre-defined profile that agrees with a tryptophanase activity profile and pyruvic acid and/or its salt is added at a predetermined time. In the process of the invention, the feeding rate of indole is a function of time and ammonium salt is fed simultaneously with indole. Preferably, pyruvic acid and/or its salt is added after 40 to 60 minutes of reaction.

Tryptophanase for use in the process of the subject invention can be produced by a tryptophanase producing microorganism such as *E. coli*. In the following examples, *E. coli* PGT 67/N 4830 was used to produce tryptophanase.

I) Fermentation of *E.coli* PGT 67/N 4830 with 5 L Fermentor

1. Culture Condition

*E.coli* PGT 67/N4830 was grown on Trp I agar plate containing 1% soypeptone, 0.5% yeast extract, 0.5% sodium chloride, 1% Tween-80, 10 mM tryptophan, 100 mg/ml ampicillin and 1.5% agar at 30° C. for overnight. A single colony was taken to inoculate into 15 ml of Trp I medium and cultivated overnight at 30° C. with vigorous shaking. Glycerol was added into the cell solution to make a final 50% concentration, then the cell solution was distributed into several small tubes (1.0 ml/tube) and stored at –70° C.

2. Fermentation in 5-Liter Fermentor:

2 ml of stock cell solution was inoculated into 200 ml of Trp I medium and cultivated overnight at 30° C. with vigorous shaking (150 rpm), then the overnight culture was transferred into 5 L fermentor containing 3.5 L Trp I medium and cultivated at 30° C. with 350 rpm. The temperature was shifted to 42° C. until the $O.D._{600}$ was near 0.6. After 5 hours the cells were centrifuged for 20 minutes at 8000 rpm and 4° C., then washed with 0 9% NaCl (cell was resuspended with 0.9% NaCl and centrifuged for 10 minutes at 16000 rpm and 4° C.) and finally stored at –20° C.

3. Fermentation in 20-L Fermentor:

7 ml of stock culture was inoculated into 700 ml of medium containing 1% Tween 80, 1% SOY-peptone peptone, 0.5% yeast extract, 0.5% NaCl, 0.01% ampicillin and 0.2% tryptophan and cultivated overnight at 30° C. Overnight culture was inoculated into 13.3 L medium and incubated at 30° C. with stirring (600 rpm), aeration was about 0.5 vvm, temperature was shifted to 42° C. when the O.D. value reached 1.2 and further cultivated for 5 hr and aeration was adjusted to 0.63 vvm (volume/volume/min). Cells were harvested by centrifuging at 6000 rpm for 20 minutes, washed with 0.9% NaCl once and then centrifuged again at 13000 rpm for 30 minutes and was stored at –20° C.

II) Preparation of Crude Enzyme Solution

Resting *E.coli* PGT 67/N4830 (10 g) was suspended into 200 ml of solution containing 3% of Tween 80, 20 mM potassium phosphate (pH 9.0) and 0.2 mM of Pyridoxal-5'-phosphate PLP and subjected to French pressure cell press.

Crude enzyme solution was obtained by centrifuging the solution at 13000 rpm for 15 min and then stored at −20° C.

III) Tryptophanase Specific Activity Assay 50 mg of cell was suspended in 1 ml of solution containing 0.2 mM of PLP, 20 mM of potassium phosphate (pH 9.0) and 3% of Tween 80 and sonicated at level 14 at 4° C. for 30 seconds and stop 1 minute, and the process was repeated for five times. The supernatant, i.e., crude enzyme extract, was obtained by centrifugation at 13000 rpm for 10 minutes. The protein concentration was determined by Bradford method (Bradford, M. B. (1976) Anal. Biochem., 72,248).

0.395 ml of distilled water and 0.1 ml of 1M potassium phosphate (pH 9.0) were mixed in a 1 ml quartz curvett and the absorbance reading was zeroed by pressing autozero button, and then to the curvett 0.5 ml of SOPC (S-O-nitrophenyl-L-cysteine) was added and mixed, reaction was started by adding 5 ml of sample and measured the change of O.D. value at 370 nm. The specific activity was defined as 1 umole substrate hydrolyzed per minute per mg protein.

IV) L-Tryptophan Synthesis

The synthesis of L-tryptophan was carried out in a batch reactor by various methods of indole feeding to accumulate high amount of L-tryptophan in a very short period of time on the basis of high enzymatic conversion from indole and sodium pyruvate.

1. Manual stepwise feeding—In experiments 1 to 3, solid indole (exps 1 & 2), or concentrated indole (4.6M in ethanol in exp 3) was manually and stepwisely fed into the reaction solution comprised 0.2 mM PLP, 20 mM potassium phosphate (pH 9.0), 3% Tween 80 and with or without addition of inosine, the reaction was carried out at 30° C. and pH 9.0.

2. Continuous feeding by manually-operated pump—In experiments 4 to 6, the conditions were the same as described in 1, except that concentrated indole (4M in ethanol) was fed into the reaction solution by manually-operated pump.

3. Computer-controlled continuous feeding by multi-slope gradient—From experiments 7 to 12, concentrated indole (4M in ethanol) was continuously fed into reaction solution controlled by a multi-slope gradient software in a computer and the typical gradient profile was shown in FIG. 1.

The conditions of experiments 1 to 12 are summarized in Table I.

TABLE I

Summary of the conditions of experiment 1 to 12

| Exp No. | Pyruvate (mM) | NH₄Cl (mM) | Ethanol (%) | Inosine (mM) |
|---|---|---|---|---|
| 1 | 500 | 600 | 5 | — |
| 2 | 100 | 300 | 5 | — |
| 3 | 400 | 500 | 4 | 400 |
| 4 | 400 | 500 | — | 350 |
| 5 | 1000 | 800 | — | 785 |
| 6 | 1000 | 1000 | — | 600 |
| 7 | 1100 | 1133 | — | 850 |
| 8 | 500 | 600 | — | 400 |

TABLE I-continued

Summary of the conditions of experiment 1 to 12

| Exp No. | Pyruvate (mM) | NH₄Cl (mM) | Ethanol (%) | Inosine (mM) |
|---|---|---|---|---|
| 9 | 1200 | 1600 | — | 1100 |
| 10 | 700 | 900 | — | 600 |
| 11 | 760 | 1270 | — | 700 |
| 12 | 1700 | 1500 | — | 1000 |

Figure 2:
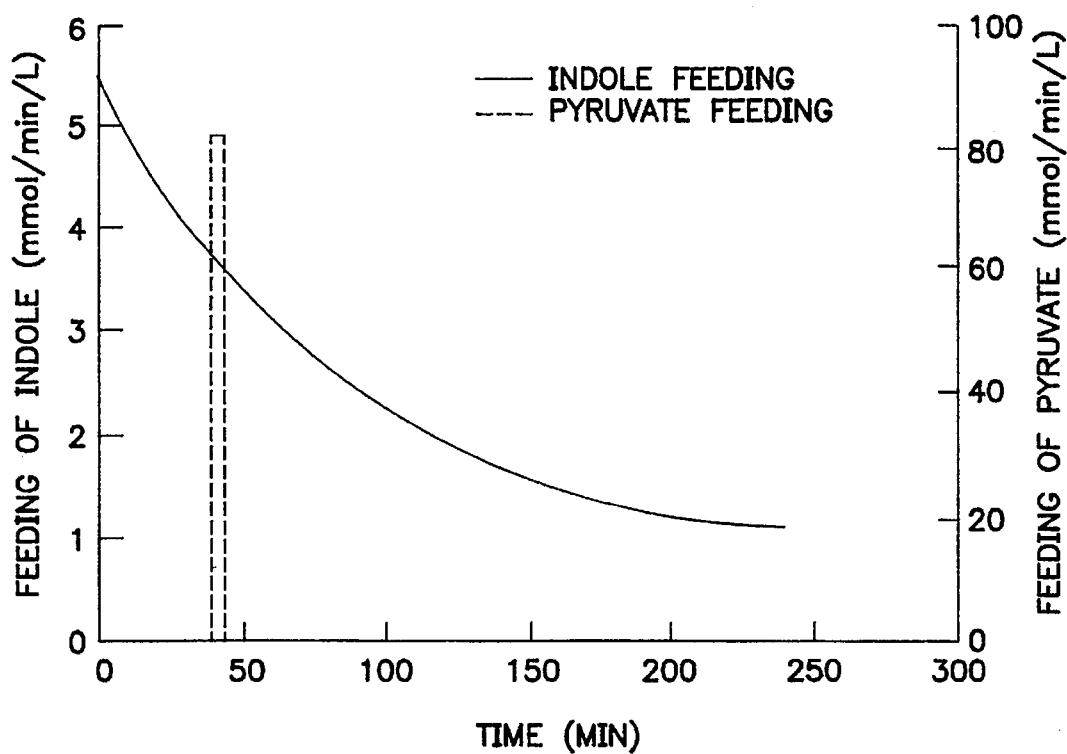
FIG. 2 shows feeding profile of substrates in enzymatic synthesis of L-tryptophan using automatic computer-controlled bioreactor. Initial conditions are as follows: 180, 300, 390 mmole of $NH_4Cl$, Na-pyruvate, and inosine, respectively; 100 mL of crude enzyme extract (15000U) and 9 mmole of L-tryptophan in 600 mL scale. The feeding of additional pyruvate was started at 40 minutes for 3.3 minutes.
Figure 3:
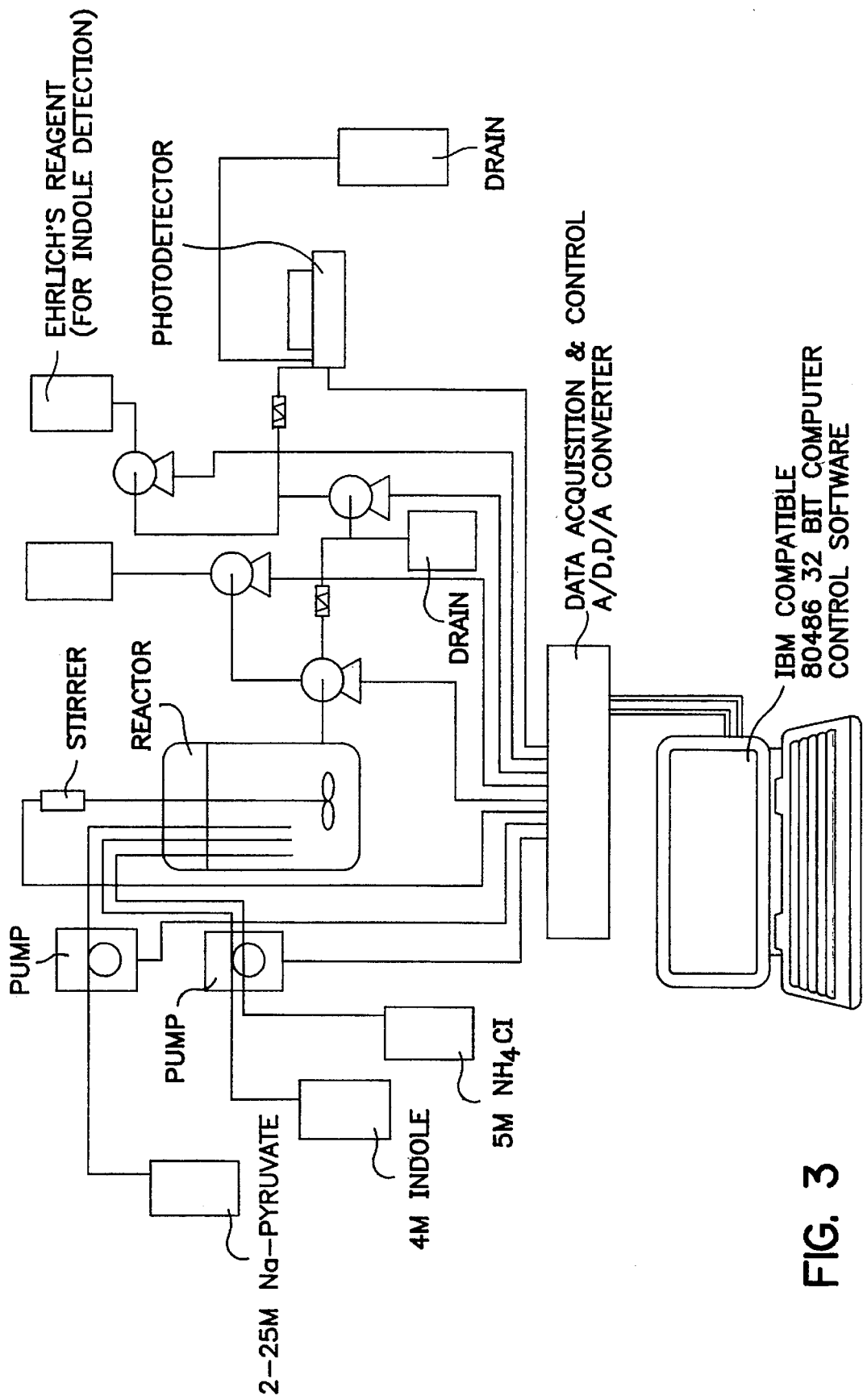
FIG. 3 shows automatic computer-controlled bioreactor system.

4. Continuous feeding with feedback control—To a 1.5 L glass reactor, 20 ml of Tween 80, 13.3 ml of 1M potassium phosphate, pH9.0, 13.3 ml of 10 mM PLP, 620 ml of distilled water and 60 ml of 5N NH₄Cl (pH was adjusted to pH 9.0 by NH₄OH) were added and then stirred well. 174.3 g (650 mmole) of inosine and 3.06 g of L-tryptophan (15 mmole) were added to the solution, reaction was started by adding 55.03 g (500 mmole) of sodium pyruvate and 166.7 ml of crude enzyme solution (150 U/ml). The solution of 5N NH₄Cl and 4M indole (prepared in ethanol) were fed into the reaction system from the beginning to the end of-the reaction according to the curve shown in FIG. 2. Additional 110 mL (270 mmole) of sodium pyruvate (2.45M aqueous solution) was supplied into the reaction solution by pump in 2 minutes after 40 minutes of reaction as shown in FIG. 2. Samples were taken at intervals to monitor the residual concentration of indole by HPLC. The reactor was designed according to the blue print in FIG. 3. After the reaction was completed, the mixture was filtered and washed with cold water to give a white solid cake which was identified as tryptophan-inosine complex.

The gradient feeding profile indicated in FIG. 2 was simulated by a computer to follow the enzyme activity decay profile and was controlled by Labtech Notebook program. The detailed equipments illustrated in FIG. 3 were as follows:

o Computer: IBM-PC compatible portable 80486-33 32 bit computer o Interfaces: High speed data acquisition board AXIOM (AX-5412-LG), channel 2 for detector signal input 8 channel D/A board (AX5212), channel 2 & 3 for feeding control of pump 1 & 2, respectively amplifier/multiplexer panel (AX-751) general purpose screw terminal panel (AX750)

o Software: LTN Labtech Notebook

•Pumps:

P1 Masterflex Drive model no. 7523-10 1–100 rpm with 7523-10 pump head (8 channel roll) for indole and NH₄Cl feeding, tubing 7624-22 (silicone) or 7605-26 (viton)

P2 Masterflex Drive model no. 7520-35 1–100 rpm with 7518-10 pump head (easy load, ss) for liquid Na-pyruvate feeding, tubing masterflex 6411-16

P3 Eyela micro tube pump MP-3

P4 Pharmacia peristaltic pump P-1

P5 Eyela micro tube pump MP-3

P6 is the same as P2

TABLE II

| Pumps | P1 | P2 | P3 | P4 | P5 | P6 |
|---|---|---|---|---|---|---|
| | • Tubing & Speed: | | | | | |
| Tubing* | 7624-22 (0.1–0.6L) 7605-26 (0.6–1L) | 96410-16 | 96410-14 | 96410-14 | 96410-14 | 96410-14 |
| Setting | Computer Controlled | Computer Controlled | 1.5 | 6 | 4 (× 10) | 1.8 |
| Flow Rate | computer controlled | computer controlled | 0.375 mL/min | 4.05 mL/min | 0.37 mL/min | 3.2 mL/min |

*all tubings were Masterflex type

The predetermined feeding rate of indole is a function of time as expressed in equation (1), and the relationship between feedback signal output of computer and optical density of photodetector is expressed in equation (3).

$$F = 5.51 - 5.44 \times 10^{-2}T + 2.79 \times 10^{-4}T^2 - 7.05 \times 10^{-7}T^3 + 7.0 \times 10^{-10}T^4 \quad (1)$$
$$S = (F \times 6 - 33.167)/3.7257 \quad (2)$$
$$S_{fb} = S + 3.492 \times O_d - 29.34 \times O_d^2 + 0.0308 \quad (3)$$

where F: feeding rate of indole (mmole/min/L)
T: reaction time (min)
S: original signal
$S_{fb}$: feedback signal
$O_d$: optical density of photodetector As shown in Table III, when using manually stepwise feeding of indole, a low concentration of L-tryptophan was obtained in exps. 1 & 2 without addition of inosine, but rather high amount of L-tryptophan was accumulated (57.2 g/L or 280 mM) in exp. 3 in the presence of inosine. With the help of multi-slope feeding of indole by computer in exps. 4 to exp. 6, the amount of L-tryptophan was obviously increased to over 122.6 g/L (600 mM) in 7 hours of reaction and gave a reasonable conversion of sodium pyruvate (about 60%). Finally, by the use of more precise indole feeding profile predetermined in accordance with the enzyme activity profile in exp. 7–12, the biosynthesis efficiency was further improved to give over 102 g/L (500 mM) of L-tryptophan in 3.5 hours of reaction (exp. 11) and maintained 70% conversion of sodium pyruvate. Also the highest amount of L-tryptophan (188.6 g/L or 923 mM) was obtained by this method in exp. 12.

Figure 4:
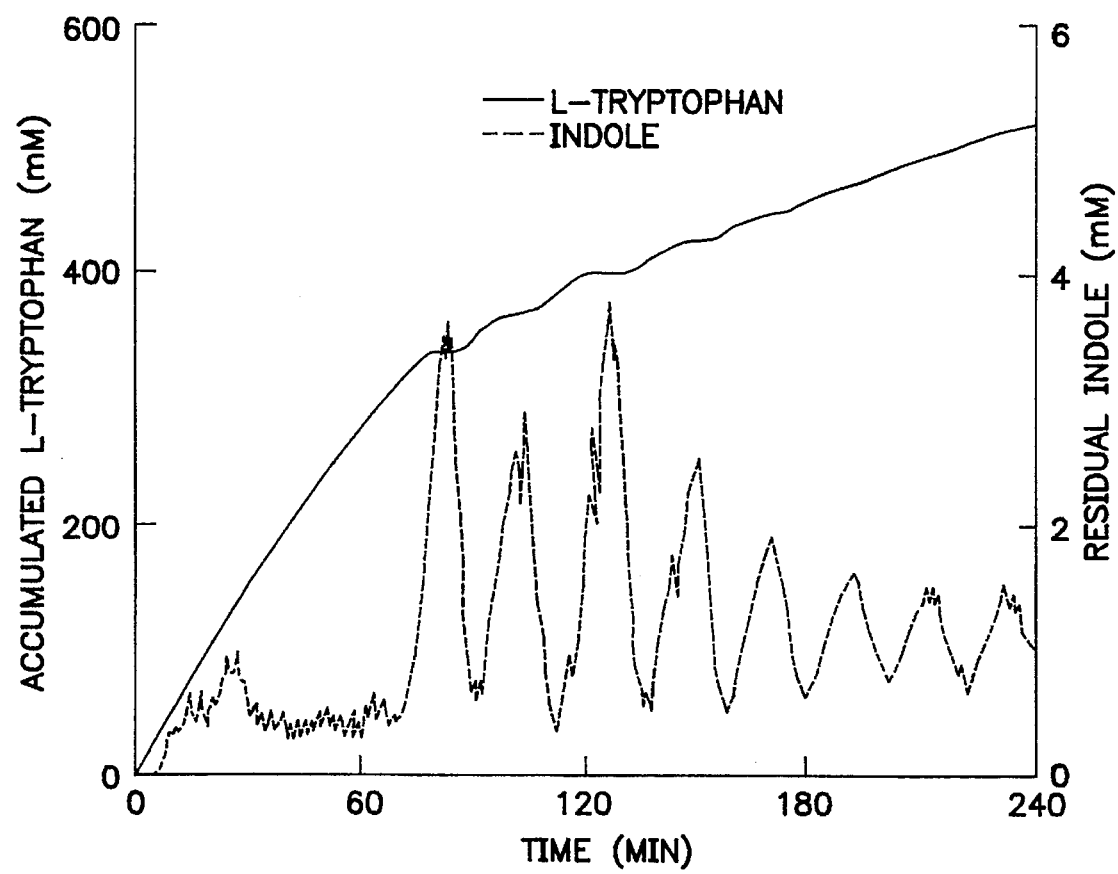
FIG. 4 shows enzymatic synthesis of L-tryptophan using automatic computer feeding and feedback-controlled by on-line indole assay.

When the indole feeding was combined with the feedback control of an on-line indole assay by photodetector, the indole in reaction mixture could be maintained below 0.59 g/L (5 mM) in entire reaction period, and finally gave a successful result that 108.3 g/L (540 mM) of L-tryptophan was accumulated while the indole concentration was maintained below 4 mM; the yield based on indole and sodium pyruvate was 99.4% and 62.7%, respectively. The experimental data were shown in FIG. 4.

TABLE III

Summary results from enzymatic synthesis of L-tryptophan under different conditions.

| Exp No. | Accu. L-Trp (g/L) | Time (min) | Pyruvate Conversion | Biocatalyst* | Scale (mL) | Temperature (°C.) | Inosine used (g/L) |
|---|---|---|---|---|---|---|---|
| 1 | 19 | 90 | 18.6 | cell/41.4 mg | 3 | 30 | — |
| 2 | 14.7 | 80 | 70.0 | cell/25 mg | 3 | 30 | — |
| 3 | 57.2 | 250 | 70.0 | cell/50 mg | 6 | 30 | 53.6 |
| 4 | 65.8 | 189 | 80.6 | enzyme/1 g | 120 | 25 | 107.3 |
| 5 | 133.2 | 420 | 59.3 | enzyme/1 g | 120 | 25 | 210.8 |
| 6 | 127.5 | 428 | 62.4 | cell/5 g | 600 | 25 | 160.9 |
| 7 | 109.3 | 377 | 53.5 | enzyme/5 g | 600 | 25 | 201.1 |
| 8 | 144.8 | 510 | 64.4 | cell/3 g | 360 | 25 | 228 |
| 9 | 174.9 | 496 | 71.3 | cell/0.83 g | 100 | 25 | 295 |
| 10 | 103.6 | 191 | 72.4 | enzyme/0.83 g | 100 | 25 | 160.9 |
| 11 | 109.5 | 220 | 70.4 | enzyme/1.3 g | 160 | 25 | 187.7 |
| 12 | 188.6 | 1173 | 61.5 | cell/0.83 g | 100 | 25 | 295 |

*cell: resting cell; enzyme: supernatant from cell-free extract

We claim:

1. An computer-controlled bioreactor system for use in an enzymatic synthesis of L-tryptophan comprising:

a bioreactor;

a stirring means;

an indole storing means;

an ammonium salt storing means;

a pyruvic acid and/or pyruvate salt storing means;

an indole and ammonium salt feeding pump with an output means from said indole and ammonium salt storing means and input means to said bioreactor;

a pyruvic acid and/or pyruvate salt feeding pump with an output means from said pyruvic acid and/or pyruvate storing means and input means to said bioreactor;

a computer with data communication means to said stirring means, said pyruvic acid and/or pyruvate salt feeding pump and said indole and said ammonium salt feeding pump;

wherein said indole and ammonium salt feeding pump and pyruvic acid and/or pyruvate salt feeding pump are operatively linked with said computer;

wherein said indole and ammonium salt feeding pump and pyruvic acid and/or pyruvate salt feeding pump and said input means are capable of inputting said indole, said pyruvic acid or pyruvic salt and said ammonium salt into a reaction solution in said computer-controlled bioreactor;

wherein said computer and data communication means controls the input of said pyruvic acid or said pyruvic salt and said ammonium salt into said bioreactor by controlling said feeding pump and input means;

wherein said bioreactor stirring means mixes said indole with either the pyruvic acid or pyruvic salt and the ammonium salt in the presence of a tryptophanase;

wherein said computer controls the feeding rate of said indole to optimize said tryptophanase's activity over time by calculating the input of said pyruvic acid or said pyruvic salt and said ammonium salt and the feeding rate of said indole according to a feeding rate of indole equation comprising:

$$F=5.51-5.44*10^{-2}T+2.79*10^{-4}T^2-7.05*10^{-7}T^3+7.0*10^{-10}T^4,$$

wherein:
F is the feeding rate of indole (mmole/min/L),
T is the reaction time of enzymatic synthesis (min); and
wherein said computer controls the addition of pyruvic acid or pyruvic salt at a predetermined time.

2. The automatic computer-controlled bioreactor system of claim 1, further comprising:
wherein the biosynthesis efficiency is about 102 g/L of L-tryptophan in 3.5 hours of reaction.

3. An computer-controlled bioreactor system for use in an enzymatic synthesis of L-tryptophan comprising:
a bioreactor;
a stirring means;
an indole storing means;
an ammonium salt storing means;
a pyruvic acid and/or pyruvate salt storing means;
an indole and ammonium salt feeding pump with an output means from said indole and ammonium salt storing means and an input means to said bioreactor;
a pyruvic acid and/or pyruvate salt feeding pump with an output means from said pyruvic acid and/or pyruvate storing means and an input means to said bioreactor;
an on-line indole assay device with an output means from said bioreactor and an input means to said on-line indole assay device;
a computer with data communication means to said stirring means, said pyruvic acid and/or pyruvate salt feeding pump and said indole and ammonium salt feeding pump, and said on-line indole assay device;
wherein said on-line indole assay device, said indole and ammonium salt feeding pump and said pyruvic acid and/or pyruvate salt feeding pump are operatively linked with said computer;
wherein said indole and ammonium salt feeding pump and pyruvic acid and/or pyruvate salt feeding pump and said input means are capable of inputting an indole, a pyruvic acid or a pyruvic salt and an ammonium salt into said reaction solution in said bioreactor;
wherein said computer and data communication means controls the input of said pyruvic acid or said pyruvic salt and said ammonium salt into said bioreactor by controlling said feeding pumps and said input means;

wherein said bioreactor stirring means mixes said indole with either the pyruvic acid or pyruvic salt and the ammonium salt in the presence of a tryptophanase;

wherein said on-line indole assay device comprises a photodetector capable of reading the optical density of a reaction solution sample obtained from said bioreactor by said output means from said bioreactor and said input means to said on-line indole assay device and wherein said on-line indole assay device reads the optical density of said reaction solution sample from said bioreactor;

wherein said on-line indole assay device is operatively linked to said computer and generates a feedback signal to said computer comprising the optical density of indole in a sample;

wherein said computer optimizes said tryptophanase's activity by calculating the input of said pyruvic acid or said pyruvic salt and said ammonium salt and said feeding rate of indole by said input pumps by using said optical density of indole feedback signal according to a feedback signal output equation comprising:

$$S_{fb}=S+3.492*O_d-29.34*O_d^2+0.0308,$$

wherein:
$S_{fb}$ is a feedback signal output,
S is an original signal,
$S=(F*6-33.167)/3.7257$,
F is a feeding rate of indole (mmole/min/L), and $$F=5.51-5.44*10^{-2}T+2.79*10^{-4}T^2-7.05*10^{-7}T^3+7.0*10^{-10}T^4,$$

T is a reaction time of the enzymatic synthesis (min),
$O_d$ is an optical density of indole; and
wherein said computer controls the addition of pyruvic acid or pyruvic salt at a predetermined time.

4. The automatic computer-controlled bioreactor system of claim 3 further comprising:
wherein said computer controls the feeding rate of indole into said reaction solution to optimize said tryptophanase's activity by optimizing said feedback signal output $S_{fb}$ according to a feedback signal output equation comprising:

$$S_{fb}=0.002-8.76*10^{-2}*T+4.49*T^2-11.35*T^3+11.27*10^{-10}*T^4+3.492*O_d-29.34*O_d^2$$

wherein:
$S_{fb}$ is the feedback signal output,
T is the reaction time of the enzymatic synthesis (min); and
$O_d$ is the optical density of indole.

5. The automatic computer-controlled bioreactor system of claim 3 further comprising:
a Ehrlich's reagent storage means with output means from said storage means and input means to said photodetector;
wherein said Ehrlich's reagent input means inputs said Ehrlich's reagent with said reaction solution sample in said photodetector;
wherein said photodetector uses said Ehrlich's reagent in said reaction solution sample to obtain an optical density, $O_d$, reading;
wherein said photodetector outputs said optical density to said computer, which calculates the concentration of said indole in said reaction solution sample.

6. The automatic computer-controlled bioreactor system of claim 3 further comprising:

wherein said computer controls said pyruvic acid and/or pyruvic salt input pump to add additional pyruvic acid and/or pyruvic salt into said bioreactor reaction solution between about 40 to about 60 minutes after said enzymatic reaction is begun.

7. The automatic computer-controlled bioreactor system of claim 3, further comprising:

wherein the biosynthesis efficiency is about 108 g/L of L-tryptophan in 3.5 hours of reaction.

8. The automatic computer-controlled bioreactor system of claim 1 or 3, further comprising:

wherein said tryptophanase is in a microorganism or a cell-free extract.

9. The automatic computer-controlled bioreactor system of claim 1 or 3, wherein said tryptophanase is produced by an *E. coli* microorganism.

10. The automatic computer-controlled bioreactor system of claim 9, wherein said *E. coli* microorganism is PGT 67/N 4830.

11. The automatic computer-controlled bioreactor system of claim 1 or 3, further comprising:

wherein an inosine is present as a precipitant for said L-tryptophan during said enzymatic synthesis.

12. The computer-controlled bioreactor system according to claim 1 or 3 wherein said ammonium salt is fed simultaneously with said indole.

13. The computer-controlled bioreactor system according to claim 1 or 3, further comprising:

wherein said pyruvic acid and/or pyruvate salt is added after about 40 to about 60 minutes of said enzymatic synthesis.

* * * * *

UNITED STATES PATENT AND TRADEMARK OFFICE
CERTIFICATE OF CORRECTION

PATENT NO. : 5,629,202
DATED : MAY 13, 1997
INVENTOR(S) : SU et al.

It is certified that error appears in the above-identified patent and that said Letters Patent is hereby corrected as shown below:

In column 2, line 62, please delete "assay." and replace therefor with -- assay--.

In column 3, line 13, please insert --indole and ammonium salt is controlled by a pre-defined-- before the word "profile".

In column 4, lines 42 and 43, please delete the spaces between "the" and "O.D.$_{600}$" (PTO).

In column 4, line 51, please delete "peptone".

In column 5, line 20, please delete "umole" and replace therefor with --μmole--

Signed and Sealed this

Twenty-fifth Day of May, 1999

Attest:

Q. TODD DICKINSON

Attesting Officer     *Acting Commissioner of Patents and Trademarks*